United States Patent [19]

Camblin

[11] Patent Number: 5,156,832
[45] Date of Patent: Oct. 20, 1992

[54] COMPOSITIONS CONTAINING CYPROCONAZOLE AND ROSE BENGAL

[75] Inventor: Philippe C. Camblin, Fournes En Weppes, France

[73] Assignee: Sandoz Ltd., Basel, Switzerland

[21] Appl. No.: 670,669

[22] Filed: Mar. 18, 1991

[51] Int. Cl.$^5$ ............ A01N 43/16; A01N 43/64; A61K 49/00
[52] U.S. Cl. ............ 424/10; 47/1.01; 514/383; 514/454
[58] Field of Search ............ 514/383, 454; 424/10; 47/1.01

[56] References Cited

U.S. PATENT DOCUMENTS 4,647,578 3/1987 Crounse et al. ............ 514/454
4,664,696 5/1987 Schaub ............ 514/383

FOREIGN PATENT DOCUMENTS 0297426 1/1989 European Pat. Off. .

Primary Examiner—Allen J. Robinson
Attorney, Agent, or Firm—Allen E. Norris

[57] ABSTRACT

Safening of the fungicide cyproconazole employing rose Bengal.

15 Claims, No Drawings

COMPOSITIONS CONTAINING CYPROCONAZOLE AND ROSE BENGAL

The present invention concerns fungicidal compositions comprising α-(4-chlorophenyl)-α-(1-cyclopropylethyl)-1H-1,2,4-triazole-1-ethanol as active ingredient.

It is known that α-(4-chlorophenyl)-α-(1-cyclopropylethyl)-1H-1,2,4-triazole-1-ethanol hereinafter referred to by its generic name cyproconazole has interesting fungicidal activity against a broad spectrum of phytopathogenic fungi such as particularly powdery mildew, rusts, scabs, Septoria, scab, Monilinia, Venturia, Cercospora, Rynchosporium, Ustilago, Tilletia and others.

It is also known e.g. from European Published Patent Application No EP 297426 that the fluorescein derivative rose Bengal (also known as rose Bengale) reduces the phytotoxicity of certain azoles in seed dressing formulations.

In the treatment of fungal disease on plants it is essential that the chosen fungicide be employed at application rates which are not phytotoxic to plants. The margin between the application rate providing substantial control of fungal infestation and the application rate causing phytotoxic symptoms to plants should therefore be sufficiently great to allow a safe and flexible antifungal treatment of plants. The objective of this invention is to provide a formulation which reduces the phytotoxicity of cyproconazole while maintaining a sufficient level of its fungicidal activity.

It has now surprisingly been found that rose Bengal also reduces the phytotoxic threshold of cyproconazole.

The invention therefore provides a fungicidal composition comprising a fungicidally effective amount of cyproconazole and rose Bengal in an amount sufficient to reduce the phytotoxicity of cyproconazole.

Cyproconazole, which has the formula

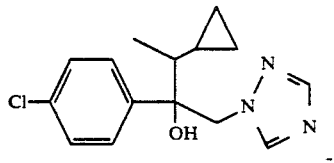

its preparation, use and formulation are known eg from U.S. Pat. No. 4,664,696 the contents of which are incorporated herein by reference.

Rose Bengal is the fluorescein derivative 4,5,6,7-tetrachloro-2',4',5',7'iodo fluorescein sodium derivative sodium salt of the formula

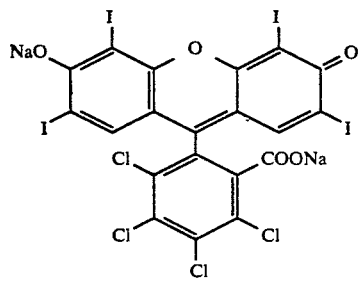

(cf Merck Index 11th ed. 1989 p. 1314). The invention is also intended to encompass the use of other salts e.g. alkali metal salts other than the disodium salt shown such as the potassium salt.

The ability of rose Bengal to reduce the phytotoxicity of (=safen) cyproconazole may be employed in various ways. For example it may enable cyproconazole to be employed as a seed dressing agent at rates which had previously been phytotoxic and thus prevented fungi which required such rates for control from being combatted or seeds of particular crops from being treated at all. This may also be viewed as broadening the effective window between the minimum application rate needed for satisfactory control of the pathogen and the maximum application rate at which no significant phytotoxicity is observed for cyproconazole.

In addition to its safening effect rose Bengal enhances the fungicidal effect of cyproconazole. This enhancing effect may also serve to allow a reduction of application rate without loss of effectiveness or to improve efficacy on fungi where less than adequate control was observed at lower rates.

The safening effect of rose Bengal on cyproconazole can be demonstrated in standard greenhouse and field tests for example employing seed treatment of cereals e.g. wheat and observing the relative inhibitory effect of cyproconazole formulations with and without rose Bengal on the emergence and growth of seeds.

These tests show a reduction of such inhibitory effect when employing rose Bengal in combination with cyproconazole.

Combined treatment according to the invention is particularly suitable for cereals especially wheat and barley.

The amount of rose Bengal and cyproconazole to be used will vary depending on a variety of factors such as crop seed used, target pathogen, soil composition, climate and the like.

In general, satisfactory effects with seed dressing applications will be obtained when employing from 0.5 gm to 75 gm, more preferably from 0.5 gm to 25 gm, of rose Bengal per 100 kg of seed. Cyproconazole will conveniently be employed in an amount of 0.5 gm to 10 gm, especially 0.5 to 5 gm per 100 kg of seed. A typical treatment would be for example with 1 g each of rose Bengal and cyproconazole per 100 kg of seed suitably formulated.

Cyproconazole and rose Bengal may be co-applied in conventional manner in the form of premixes, tank mixes or by sequential treatment. Application is conveniently in the form of a suitable seed treatment formulation eg as an aqueous dispersion or as a dry powder having good adherence to the seeds whereby liquid formulations are preferred.

Suitable seed dressing formulations may be obtained in conventional manner, by mixing appropriate amounts of cyproconazole and rose Bengal and agriculturally acceptable diluents or carriers eg as described in U.S. Pat. No. 4,664,696.

The amount of active ingredient contained in such formulations will depend on seeds to be treated, method of treatment and the like. In general formulation will contain 0.2 to 30, especially 0.2 to 10% w/w of rose Bengal and 0.2 to 12, especially 0.2 to 6% w/w of cyproconazole.

A typical example for the preparation of a seed dressing formulation is as follows.

EXAMPLE 1

Seed Dressing Formulation

| Ingredients (% w/w) | | |
|---|---|---|
| i) Cyproconazole 10% WG | 4.0 | (= 0.4 cyproconazole a.i.) |
| ii) KELZAN ® | 0.3 | |
| iii) PROXCEL GXL | 0.1 | |
| iv) PLURONIC ® P105 | 2.0 | |
| v) Dist. Water | 78.05 | |
| vi) Urea | 5.0 | |
| vii) Sunspray GE oil | 10.0 | |
| viii) rose Bengal (sodium salt) | 0.5 | |
| ix) DREWPLUS ® L-768 | 0.05 | |

Kelzan and Proxcel GXL are added to the dist. water and osterized until dissolved. The cyproconazole is then added and osterized at 30% power for 5 min. The remaining ingredients are added and osterized for a final 5 min. at 30% power.

ii) polysaccharide gum; Kelco, San Diego, CA iii) 1,2-benzisothiazolin-3-one, NaOH, dipropylene glycol, H₂O; ICI, Wilmington, DE iv) polyglycol; BASF, Parsippany, NJ vii)

viii) Pylam Products Co. Ltd., Garden City, NY 11530 ix) Silicone ant-foramant; DREW-AMEROLD, Boonton, NJ

What is claimed is:

1. A fungicidal composition comprising a fungicidally effective amount of cyproconazole and rose Bengal in an amount effective for reducing the phytotoxicity of cyproconazole.

2. A composition according to claim 1 wherein rose Bengal is in its di-sodium form.

3. A composition according to claim 1 comprising 0.2 to 12% w/w of cyproconazole and 0.2 to 30% w/w of rose Bengal.

4. A composition according to claim 1 comprising 0.2 to 6% w/w of cyproconazole and 0.2 to 10% w/w of rose Bengal.

5. A method of coating seeds to suppress fungal diseases which comprises applying to the seeds an effective amount of a composition comprising a fungicidally effective amount of cyproconazole and rose Bengal in an amount effective for reducing the phytotoxicity of cyproconazole.

6. A method according to claim 5 wherein rose Bengal is in its disodium form.

7. A method according to claim 5 wherein the composition comprises 0.2 to 12% w/w of cyproconazole and 0.2 to 3% w/w of rose Bengal.

8. A method according to claim 5 wherein the composition comprises 0.2 to 6% w/w of cyproconazole and 0.2 to 10% w/w of rose Bengal.

9. A method of suppressing fungal diseases of plants which comprises co-applying to the seeds of said plants a fungicidally effective amount of cyproconazole and rose Bengal in an amount effective for reducing the phytotoxicity of cyproconazole on that plant.

10. A method according to claim 9 wherein rose Bengal is in the disodium form.

11. A method according to claim 9 which comprises co-applying from 0.5 gm to 10 gm of cyproconazole and 0.5 gm to 75 gm of rose Bengal per 100 kg of seeds.

12. A method according to claim 9 which comprises co-applying from 0.5 gm to 5 gm of cyproconazole and 0.5 gm to 25 gm of rose Bengal per 100 kg of seeds.

13. A method according to claim 9 wherein the seed is a cereal.

14. A method according to claim 9 wherein the seed is of wheat.

15. Seeds coated with fungicidally effective amount of cyproconazole and an amount of rose Bengal effective for reducing the phytotoxicity of cyproconazole.

* * * * *